US011191643B2

(12) United States Patent
Vola et al.

(10) Patent No.: US 11,191,643 B2
(45) Date of Patent: Dec. 7, 2021

(54) DEVICE FOR REPAIR OF THE CORDS OF THE MITRAL VALVE OF A HEART BY TRANSFEMORAL APPROACH

(71) Applicants: CMI'NOV, Monistrol-sur-Loire (FR); Marco Vola, Saint-Priest-en Jarez (FR)

(72) Inventors: Marco Vola, Saint-Priest-en Jarez (FR); Bernard Pain, Monistrol-sur-Loire (FR)

(73) Assignees: CMI'NOV, Monistrol-sur-Loire (FR); Marco Vola, Saint-Priest-en Jarez (FR)

( * ) Notice: Subject to any disclaimer, the term of this patent is extended or adjusted under 35 U.S.C. 154(b) by 42 days.

(21) Appl. No.: 16/493,315

(22) PCT Filed: Feb. 1, 2018

(86) PCT No.: PCT/FR2018/050243
§ 371 (c)(1),
(2) Date: Sep. 12, 2019

(87) PCT Pub. No.: WO2018/167388
PCT Pub. Date: Sep. 20, 2018

(65) Prior Publication Data
US 2020/0085577 A1   Mar. 19, 2020

(30) Foreign Application Priority Data

Mar. 13, 2017   (FR) ..................... 1752019

(51) Int. Cl.
*A61F 2/24* (2006.01)
*A61B 17/068* (2006.01)

(52) U.S. Cl.
CPC .......... *A61F 2/2466* (2013.01); *A61B 17/068* (2013.01); *A61F 2/2457* (2013.01); *A61F 2220/0016* (2013.01)

(58) Field of Classification Search
CPC ....... A61B 17/128; A61B 17/22; A61B 90/00; A61B 17/068; A61B 17/1285;
(Continued)

(56) References Cited

U.S. PATENT DOCUMENTS

2016/0345959 A1   12/2016   Sauer
2019/0183480 A1*   6/2019   Hiorth ................... A61F 2/2466

FOREIGN PATENT DOCUMENTS

| WO | WO 2011/067770 | 6/2011 |
| WO | WO 2013/112795 | 8/2013 |
| WO | WO 2016/042022 | 3/2016 |

OTHER PUBLICATIONS

International Search Report and the Written Opinion dated Jun. 13, 2018 From the International Searching Authority Re. Application No. PCT/FR2018/050243 and Its Translation of Search Report Into English. (13 Pages).
(Continued)

*Primary Examiner* — George J Ulsh (57) ABSTRACT

The device (1) comprises:
A first assembly (6) engageable with a handle under the control of control means for the actuation of the assembly for the placement and attachment of an artificial cord (7) on the papillary muscle (8) of a ruptured cord, said assembly is arranged at the end of a manipulation rod and comprises an elastic staple (9) connected pivotably and removably at the end of the rod so as to pass, under the action of the control means, from a position folded back along the rod to a position swung angularly relative to the rod for coming into place perpendicularly in front of the papillary muscle where the cord must be replaced, the first assembly (6) comprises means for opening the staple (9) in order to, under the action of the command means, anchor the papillary muscle (8) for the ruptured cord, the first
(Continued)

assembly (6) comprises means for unlocking with which, under the action of the command means, to release the staple (9), said staple (9) being connected to an artificial cord (7) which goes back in the rod;

A second assembly (13) engageable with a handle under the control of control means for the actuation of the assembly for the placement and attachment of the artificial cord (7) to a leaflet (2*a*) of the valve (2), the second assembly (13) is arranged at the end of the manipulation rod and comprises attachment means (9, 16) intended to slide along the artificial cord (7) and pivotably connected to the end of the rod so as to pass, under the action of the control means, from a position folded back along the rod to a position orthogonal to the rod, where the means of attachment (9, 16) are able, under the action of the command means, to attach the artificial cord (7) to said leaflet (2*a*).

20 Claims, 7 Drawing Sheets

(58) Field of Classification Search
CPC  A61B 2017/00243; A61B 2017/00867; A61B 2017/0409; A61B 2017/0464; A61B 17/1227; A61B 90/39; A61B 2090/3966; A61F 2/24; A61F 2/2457; A61F 2/2466; A61F 2220/0016
See application file for complete search history.

(56) References Cited

OTHER PUBLICATIONS

Bajona et al. "Beating-Heart, Off-Pump Mitral Valve Repair by Implantation of Artificial Chordae Tendineae: An Acute In Vivo Animal Study", Journal of Thoracic and Cardiovascular Surgery, XP025871792, 137(1): 188-193, Jan. 2009.

* cited by examiner

DEVICE FOR REPAIR OF THE CORDS OF THE MITRAL VALVE OF A HEART BY TRANSFEMORAL APPROACH

RELATED APPLICATIONS

This application is a National Phase of PCT Patent Application No. PCT/FR2018/050243 having International filing date of Feb. 1, 2018, which claims the benefit of priority of French Patent Application No. 1752019 filed on Mar. 13, 2017. The contents of the above applications are all incorporated by reference as if fully set forth herein in their entirety.

FIELD AND BACKGROUND OF THE INVENTION

The invention relates to a device for repair of the cords of the mitral valve of a heart, in particular by transfemoral approach, for example in case of mitral prolapse.

The treatment of mitral prolapse, related in particular to the elongation or rupture of one or more cords connecting the mitral valve to the papillary muscles of the heart, is a long and major operation which requires opening of the heart chambers and the rib cage, and an extracorporeal blood circulation. The operation consists in particular of replacing the defective cord, meaning attaching an artificial cord between a mitral valve leaflet and the papillary muscles of the mitral subvalvular apparatus or the apical part of the heart.

The known solution from the state of the art consists of using devices which can implant artificial cords on the edges of the swinging valves by trans-apical approach, meaning using a device intended to be positioned in a sealed inserter arranged in the chest cavity between two ribs for entering into the left ventricle by passing through the apex of the heart.

This device can further be improved, in particular by avoiding piercing the cardiac apex and reducing the invasiveness of the surgical operation done with this type of device.

SUMMARY OF THE INVENTION

The goal of the invention is to remedy these disadvantages of the prior art simply, safely, effectively, and rationally.

The problem that the invention proposes to resolve is to make the operation to repair the mitral valve cords of a heart easier, by transfemoral approach and without puncturing the artery, but instead the femoral vein.

For this purpose a device was developed to repair the mitral valve cords of the heart by transfemoral approach, and intended to be positioned in a sealed inserter arranged in a femoral vein in order to go into the left atrium of the heart by going through the wall of the septum which separates the right and left atrium.

According to the invention, this device comprises:

A first assembly engageable with a handle under the control of control means for the actuation of the assembly for the placement and attachment of an artificial cord on the papillary muscle of a ruptured or pathologically elongated cord, said assembly is arranged at the end of a manipulation rod and comprises an elastic staple connected pivotably and removably at the end of the rod so as to pass, under the action of the control means, from a position folded back along the rod to a position swung angularly relative to the rod for coming into place perpendicularly in front of the papillary muscle where the cord must be replaced, the first assembly comprises means for opening the staple in order to, under the action of the command means, staple the papillary muscle for the ruptured cord (either by simple compression of two arms with irregular surface, or by compression of two teeth of the staple which contain ends perforating the papillary muscle, partially or totally transfixing it), the first assembly comprises means for unlocking with which, under the action of the command means, to release the staple, said staple being connected to an artificial cord which goes back in the rod;

A second assembly engageable with a handle under the control of control means for the actuation of the assembly for the placement and attachment of the artificial cord to a leaflet of the valve, the second assembly is arranged at the end of the manipulation rod and comprises attachment means intended to slide along the artificial cord and pivotably connected to the end of the rod so as to pass, under the action of the control means, from a position folded back along the rod to a position swung angularly relative to the rod for placing parallel to the mitral leaflet, where the means of attachment are able, under the action of the command means, to attach the artificial cord to said leaflet.

In this way, and advantageously, the device according to the invention, in combination with a handle and means of actuation which are not part of the invention, serves to implement the operation for repair of a mitral valve cord by transfemoral approach by going up the vena cava. The active assemblies of the device navigate through the vena cava where blood pressure is relatively low.

According to a second embodiment, the means of attachment comprise an openable, repositionable and removable elastic staple, means for opening the staple, and means for unlocking the staple similar to those from the first assembly. The staple from the second assembly is intended to anchor itself in the leaflet for attaching the artificial cord there.

The artificial cord for example has the form of a non-resorbable suture thread of polyamide or Teflon.

The artificial cord can be notched, and the staple from the second assembly comprises means for sliding on the notched artificial cord only in the direction of the staple from the first assembly.

According to another embodiment, the staple from the second assembly comprises a thread intended to form an attachment loop around the artificial cord, where the artificial cord is knottable around said loop.

Advantageously, the second assembly comprises a stabilizing clip connected pivotably to the end of the rod so as to pass, under the action of the control means, from a position folded back along the rod to a position swung angularly to the rod to come parallel to the plane of the leaflet, and from an open position to a closed position for clamping and stabilizing the leaflet in order for stapling.

According to another specific embodiment, the attachment means comprise a clip connected pivotably to the end of the rod so as to pass, under the action of the control means, from a position folded back along the rod to a position swung angularly to the rod to come parallel to the plane of the tissue of the leaflet, and from an open position to a closed position for clamping the leaflet. The second assembly comprises a mobile needle that, under the action of the control means, pierces the leaflet through an opening in the clip and attaches the artificial cord to the leaflet.

Preferably, the needle comprises inside thereof a shape memory suture that can be extracted to form a loop for attaching the artificial cord to the leaflet.

According to another specific embodiment, the needle comprises means for grasping the artificial cord after having pierced the leaflet.

According to a specific embodiment, the staple comprises two elastic branches brought towards each other with hooked end parts. The opening/unlocking means comprise two arms arranged between the elastic branches of the staple and articulated around a pivot so as to pass, under the action of the control means, from a position brought close to each other to a separated position by forcing the separation of the branches of the staple to cause opening thereof. The two arms are retractable to allow the release of the removable staple.

Preferably, the clip comprises an upper jaw and a lower jaw, with openings for the passage of the needle. The lower jaw comprises a flap intended to adopt a closed position for holding the artificial cord while allowing the sliding of the clip around and along said artificial cord, and an open position for release of the artificial cord.

Preferably, and to make the surgical operation easier, the staple and the attachment means are radio opaque or else each comprises one or more radio opaque and/or ultrasound marker(s). They can also incorporate magnets to make navigation in the presence of a specifically generated magnetic field easier.

Advantageously and to improve the rehabilitation of the human tissue, the staple(s) have textile sheaths.

BRIEF DESCRIPTION OF THE SEVERAL VIEWS OF THE DRAWINGS

Further characteristics and advantages of the invention will become apparent from the description provided below, which is for reference only and is in no way restrictive, with reference to the accompanying figures, wherein.

DESCRIPTION OF SPECIFIC EMBODIMENTS OF THE INVENTION

The invention relates to a device (1) with which to perform a surgical operation consisting of repairing ruptured or elongated cords of a mitral valve (2), for example in the case of a mitral prolapse.

The device (1) is intended to be positioned in a sealed inserter of any known and appropriate type (not shown) and of a diameter less than or equal to 12 mm, placed in a femoral vein to ascend and penetrate the left atrium (3) of a heart (4) through the septal wall thereof.

Referring to FIGS. 1 to 8, the device (1) comprises a first manipulation rod (5), at the end of which is arranged a first assembly (6) for the placement and attachment of an artificial cord (7) on the papillary muscle (8) of a ruptured cord. The other end of the first rod (5) is intended to engage with a handle under the control of control means, not shown, for example in the form of a trigger, to operate the first assembly (6). The device (1) according to the invention allows, under ultrasound and possibly also radiographic control, after ascending through the vena cava, the first assembly (6) to penetrate into the left atrium (3) of the heart (4) by passing through the septal wall. Next, when the first assembly (6) is located in the left atrium (3) of the heart (4), it is able to pass through the mitral valve (2) to come facing the papillary muscle (8) for the ruptured cord (see FIG. 2). The carrier catheter can be temporarily stiffened with the ideal curvature for working across from the plane of the mitral valve.

The head of the first rod (5), made up for example of an atraumatic nose, is retractable to let an elastic staple (9) connected pivotably and removably to the end of the rod (5) appear inside. The elastic staple (9), under control of the control means from the handle, is able to pass, under the action of said control means, from a position folded back along the rod (see FIGS. 2 and 6) to a position swung orthogonally (see FIGS. 3, 4, 7 and 8). For this purpose, the elastic staple (9) is received in a base (10), itself mounted pivoting around an axis (11), under the actuation of the control means. These control means, not shown, comprise for example sets of cables connected to a part of the base (10), opposite the staple (9), to exert traction or pressure on this rear part and pivot the base (10) around the axis (11) thereof.

Figure 6:
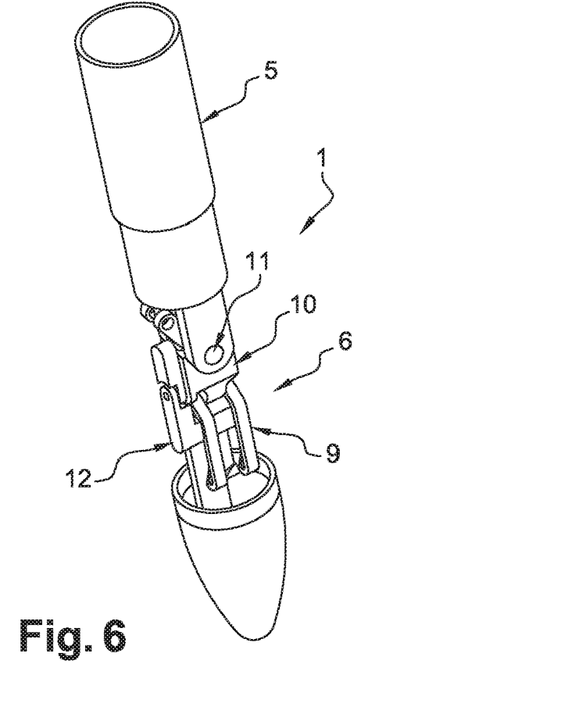
FIG. 6 is a detailed view of the end of the rod from the first assembly according to the invention, with the head retracted and the staple in folded back position.
Figure 7:
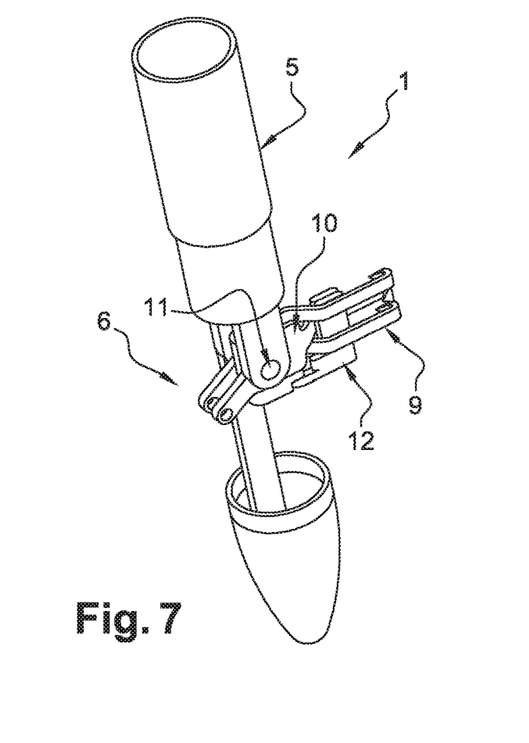
FIG. 7 is a view similar to that of FIG. 6, with the staple swung into a position orthogonal to the rod, and in closed position.
Figure 8:
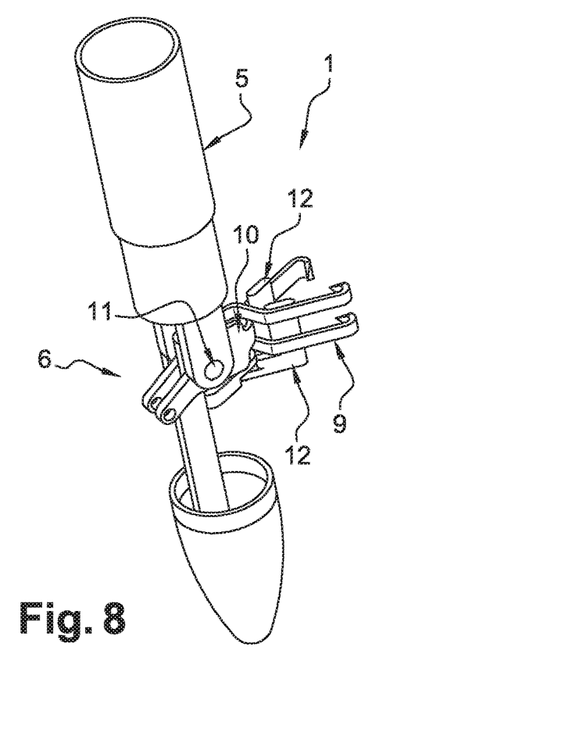
FIG. 8 is a view similar to that of FIG. 7, where the staple is shown in open position.
Figure 9:
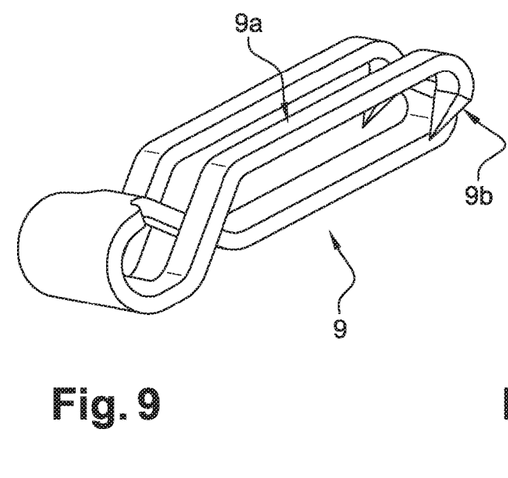
FIG. 9 is a detailed perspective view showing the staple used for anchoring the cord to the papillary muscle.
Figure 10:
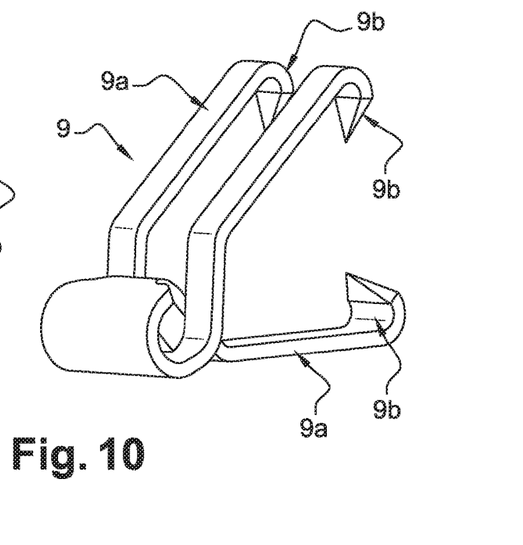
FIG. 10 is a view similar to that of FIG. 9, where the staple is shown in open position.
Figure 15:
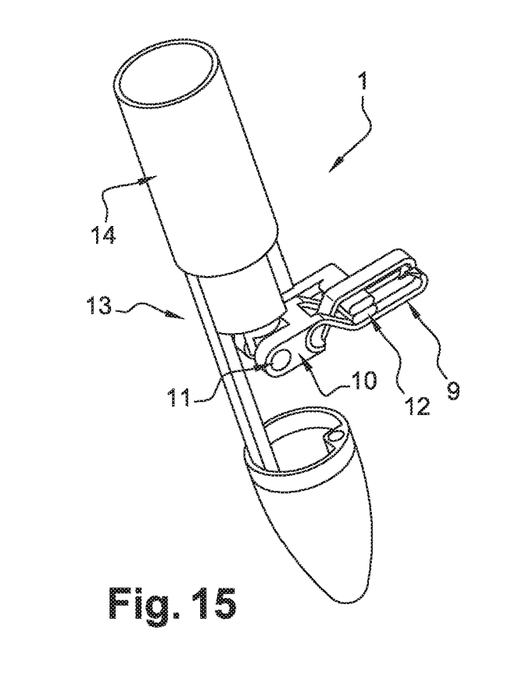
FIG. 15 is a perspective view showing the end of the manipulation rod of the second assembly, with the staple in swung position and open.
Figure 16:
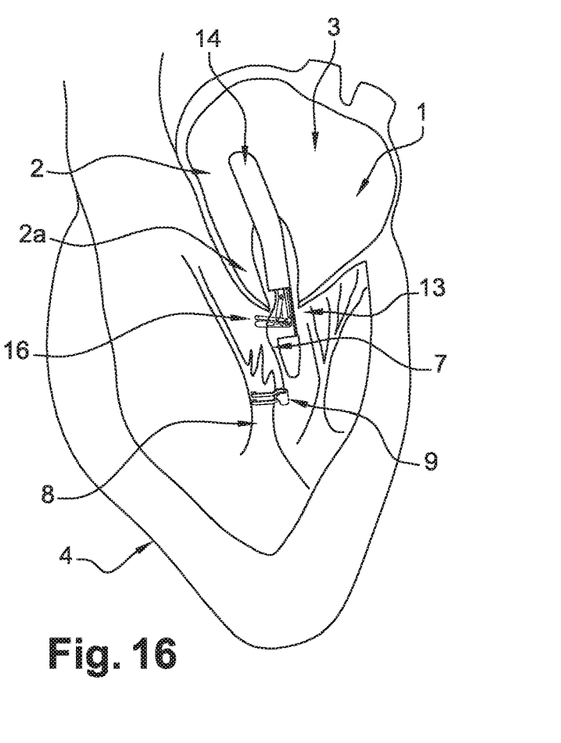
FIG. 16 is a schematic representation of a second embodiment, comprising an end rod of the second assembly having passed through the mitral valve of the heart, and illustrating a clip swung in angular position relative to the rod and having slid along the artificial cord connected to the first staple.
Figure 17:
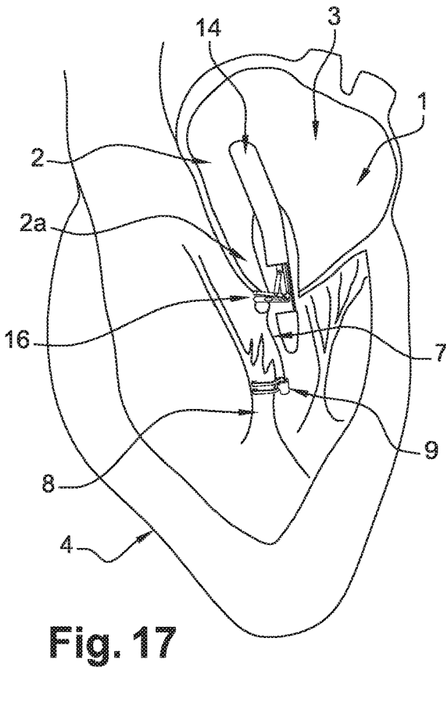
FIG. 17 is a view similar to that of FIG. 16, where the clip has clamped the mitral valve leaflet.
Figure 18:
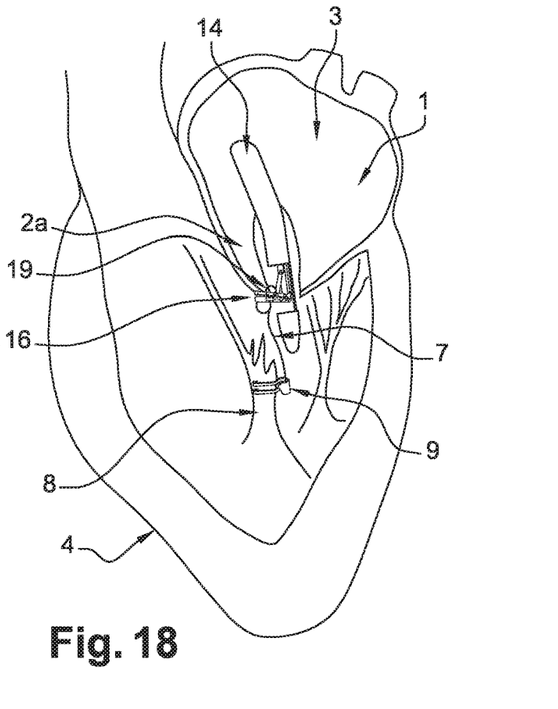
FIG. 18 is a view similar to that of FIG. 17, where a suture was released to form a loop with which to attach the artificial cord to the leaflet.
Figure 19:
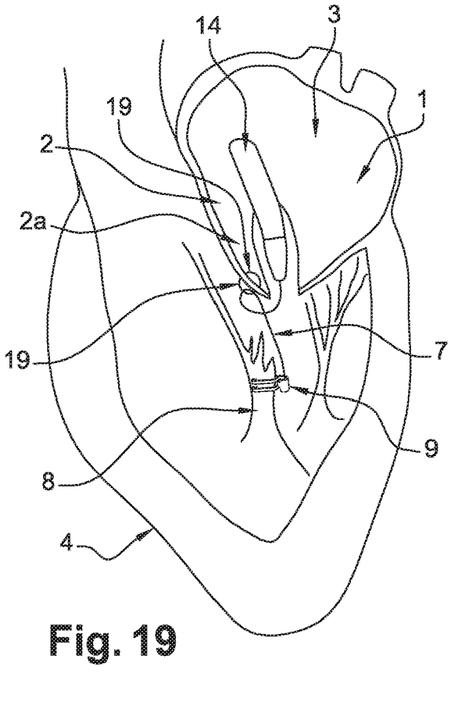
FIG. 19 is a view similar to that of FIG. 18, where the manipulation rod of the second assembly is shown being withdrawn.
Figure 20:
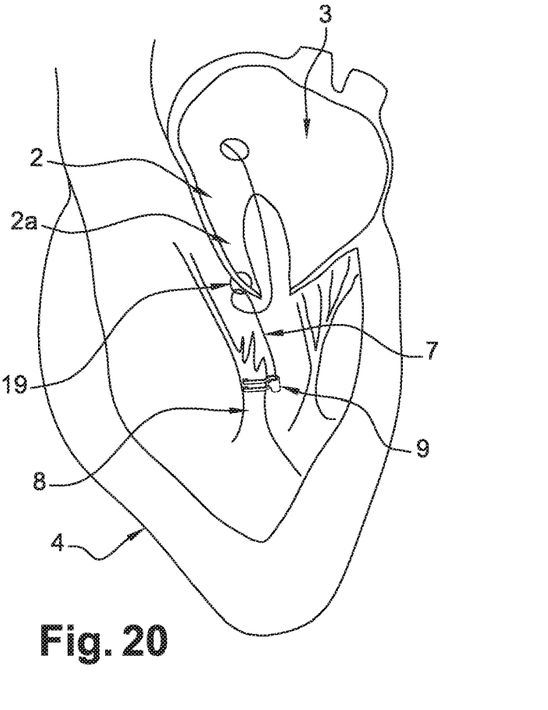
FIG. 20 is a view similar to that of FIG. 19 showing the artificial cord attached to the papillary muscle of the cord and the leaflet of the valve via the suture, before the step consisting of knotting and tensioning said artificial cord for finishing the operation.
Figure 21:
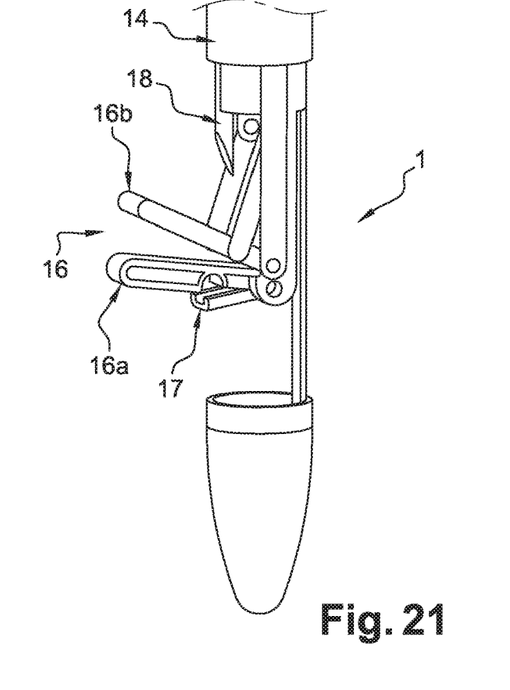
FIG. 21 is a perspective schematic representation of the clip from the second assembly according to the second embodiment, intended to attach the artificial cord to the leaflet of the valve.
Figure 22:
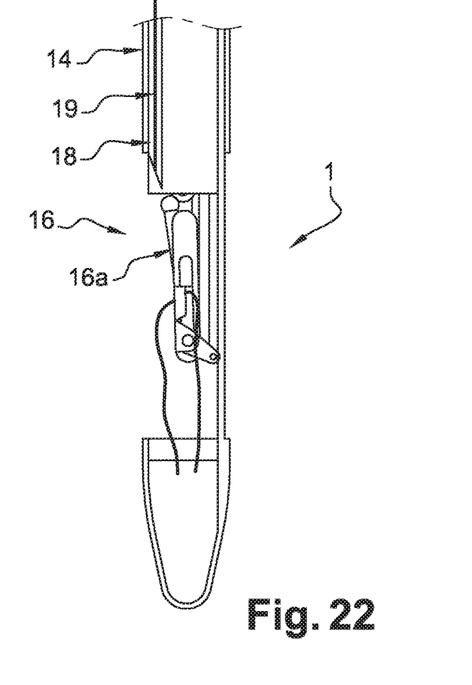
FIG. 22 is a schematic representation of the manipulation rod from the second assembly according to the second embodiment, where the clip is shown in position folded back along the rod.
Figure 23:
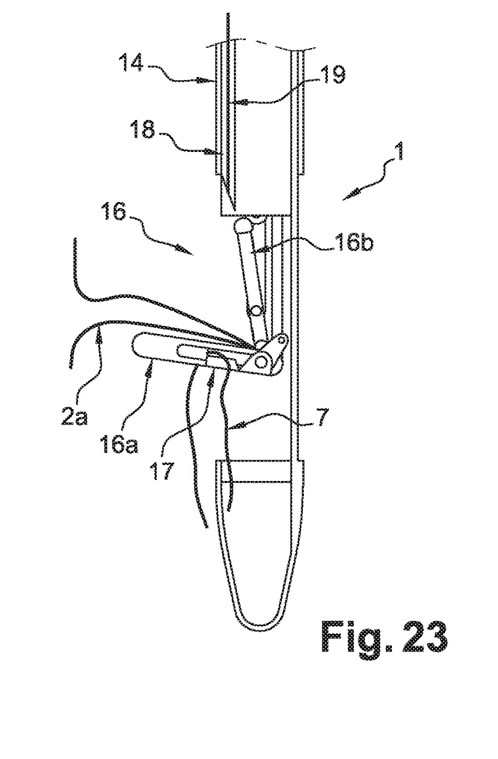
FIG. 23 is a view similar to FIG. 22, where the clip has swung angularly relative to the rod and is shown in open position, in particular with the lower jaw of the clip positioned under the leaflet of the mitral valve.
Figure 24:
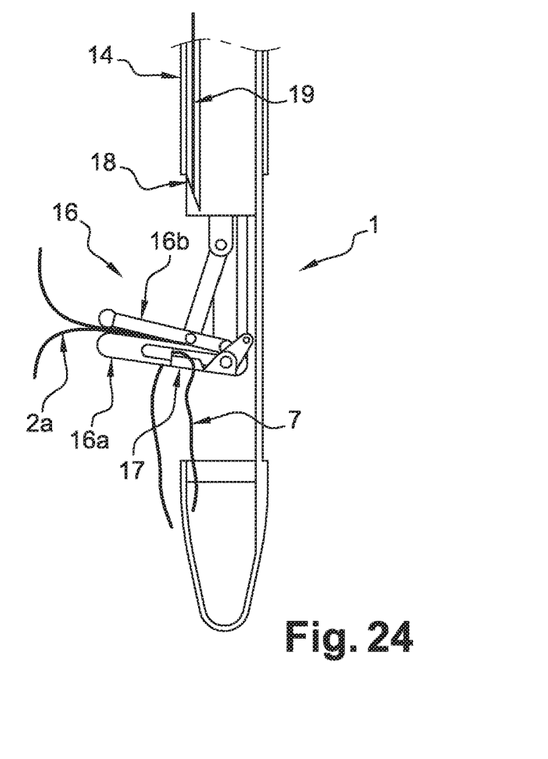
FIG. 24 is a schematic representation similar to that of FIG. 23, where the clip is represented in closed position and in position for clamping the leaflet of the valve.

Referring to FIGS. 9 and 10, the staple (9) comprises two elastic branches (9a), brought close to each other, with hooked end parts (9b) for anchoring as such. Referring to FIGS. 6 to 8, the staple (9) is held in the base (10) via two arms (12) arranged between the elastic branches (9a) of the staple (9), and articulated around a pivot, in particular around the axis (11) so as to pass, under the action of the control means, from a position brought close to each other (see FIGS. 6, 7 and 15) to a separated position by forcing the separation of the branches (9a) of the staple (9) for causing opening thereof. The pivoting of the arms (12) is done by pivoting the base (10).

Figure 1:
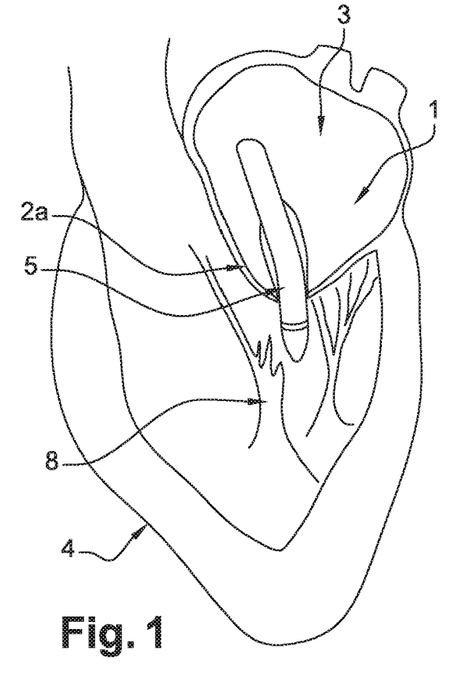
FIG. 1 shows a heart and the insertion, in the left atrium of the heart and through the mitral valve, of the manipulation rod of a first assembly that comprises the device according to the invention.
Figure 2:
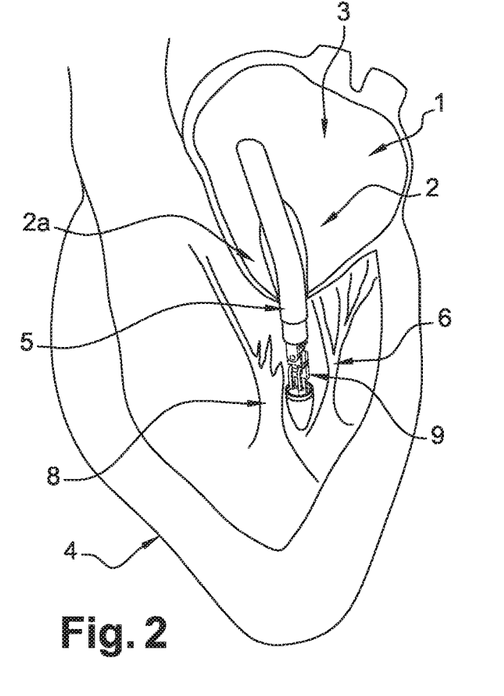
FIG. 2 is a view similar to that of FIG. 1 where the head of the rod is retracted to allow an elastic staple in folded back position to appear.
Figure 3:
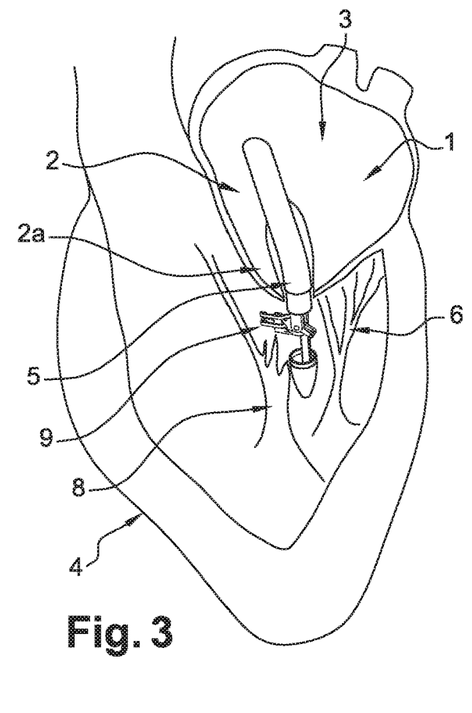
FIG. 3 is a view similar to that of FIG. 2, where the staple is swung into a position orthogonal to the rod.
Figure 4:
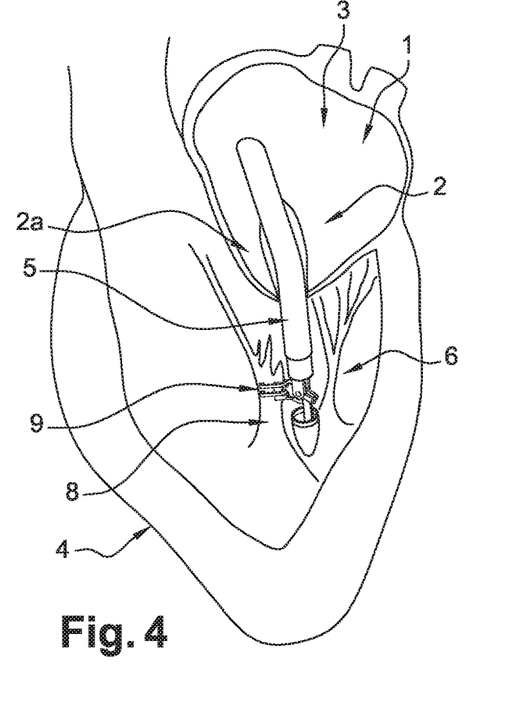
FIG. 4 is a view similar to that of FIG. 3, where the staple has come to anchor on the papillary muscle for the ruptured cord to be repaired.
Figure 5:
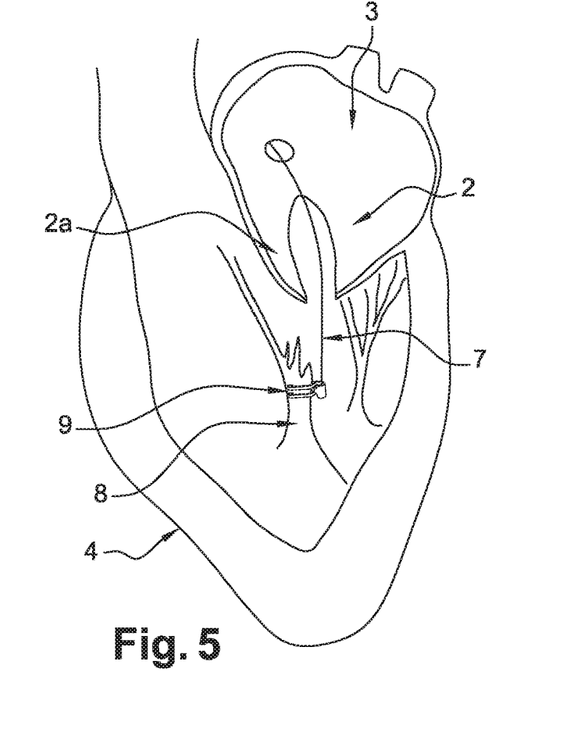
FIG. 5 is a view similar to that of FIG. 4, where the rod from the first assembly has been withdrawn so as to leave an artificial cord attached to the staple.

The gripping of the staple (9) on the papillary muscle (8) for the ruptured cord (see FIG. 4) makes it possible to keep a sufficient separation between the elastic branches (9a) of the staple (9), creating a play relative to the arms (12) which constitute means of opening and unlocking the staple (9), allowing said arms (12) to retract and release the removable staple (9) (see FIG. 5).

Referring to FIG. 5, the artificial cord (7) is now added to the staple (9) and goes up inside the first rod (5) such that after withdrawing the said rod, the artificial cord (7) goes back up along the femoral vein.

Referring to FIGS. 12 to 28, the device (1) according to the invention also comprises a second assembly (13) engageable with a handle, which can be the same handle as the one for the first assembly (6), under control of control means for the actuation of this second assembly (13) for the placement and the attachment of the artificial cord (7) to a leaflet (2a) of the valve (2).

In the same way as for the first assembly (6), the second assembly (13) is intended to go back up the vena cava, and enter into the left atrium (3) of the heart (4) by passing through the septal wall, in particular by following and sliding along the artificial cord (7) already present.

Figure 11:
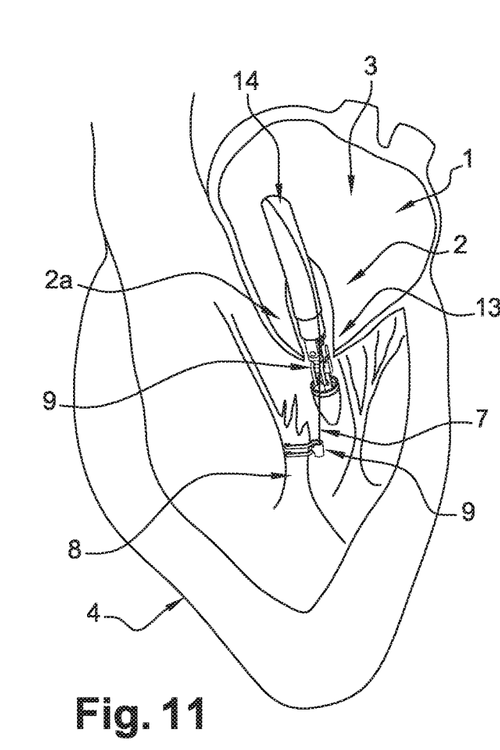
FIG. 11 is a representation of a first embodiment for the attachment of the artificial cord to the mitral valve leaflet and shows the manipulation rod of the second assembly having passed through the mitral valve with the head of the rod having been retracted to let a second staple appear in position folded back along the rod.
Figure 12:
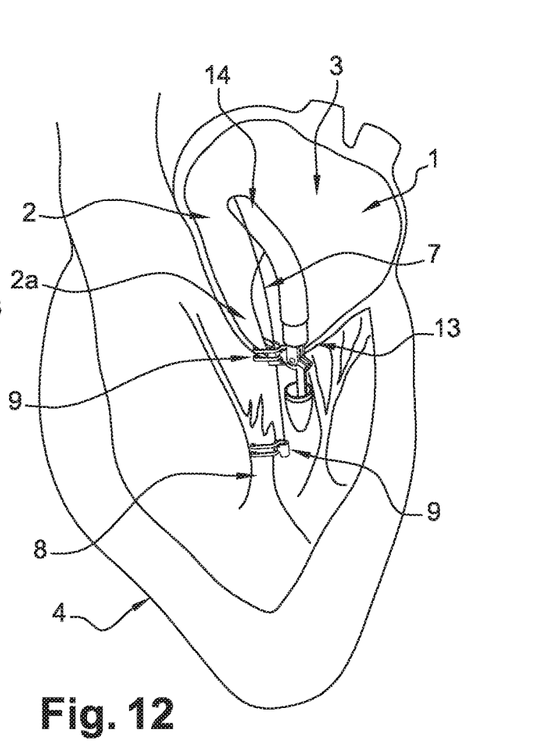
FIG. 12 is a view similar to that of FIG. 11, where the staple has swung into a position orthogonal to the rod, and the staple has slid along the artificial cord.
Figure 13:
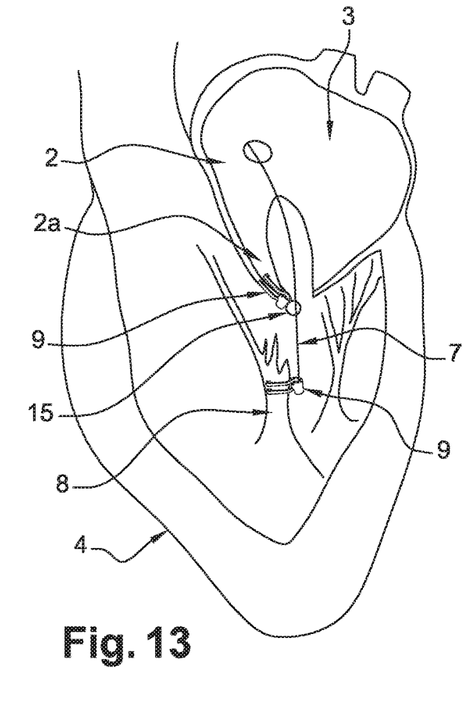
FIG. 13 shows the anchoring of the staple to the mitral valve leaflet and the release of said staple, which is connected to the artificial cord.
Figure 14:
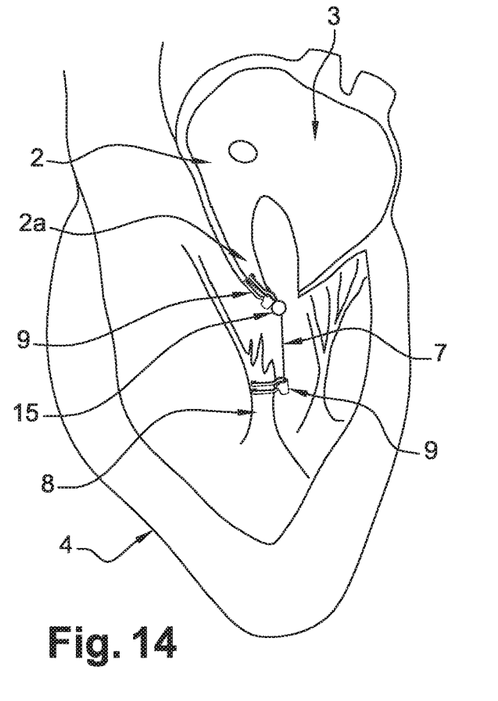
FIG. 14 is a view similar to that of FIG. 13, where the cord has been knotted around the loop that the second staple has; the cord replacement operation is completed.

The second assembly (13) is arranged at the end of the second manipulation rod (14) and comprises attachment means (9, 16), connected pivotably to the end of the rod so as to pass, under the action of the control means, from a position folded back along the rod (14) (see FIG. 11) to a position swung (see FIGS. 12, 15 to 18, 21 and 23 to 27) for attaching the artificial cord (7) to the leaflet (2a) of the valve (2).

Starting from this concept, several embodiments of the invention can be imagined.

According to a first embodiment, in particular shown in FIGS. 11 to 15, the attachment means of the artificial cord (7) to the leaflet (2a) have the shape of the staple (9), similar to the one from the first assembly (6), and which is intended to anchor onto the papillary muscle (8) for the ruptured cord. Similarly, this second staple (9) is received in a base (10) mounted pivoting around an axis (11) to pass from a position folded back along the second rod (14) (see FIG. 11) to a position swung angularly (see FIGS. 12, 15) in order to come anchor on the leaflet (2a) of the mitral valve (2). Arms (12) are arranged between the elastic branches (9a) of this second staple (9), to form means for locking and unlocking in the same way as with the first staple (9). The second staple (9) is therefore designed to open and come to anchor on the leaflet (2a). When the staple (9) is anchored on the leaflet (2a), the arms (12) can retract to release said staple (9).

The second staple (9) is connected to the artificial cord (7). To do that, and with reference to FIGS. 13 and 14, the second staple (9) comprises, for example, a thread (15) which forms a loop around the artificial cord (7). With this loop, said second staple (9) and the second assembly (13) can slide along the artificial cord (7). In this configuration, the artificial cord (7) can be knotted around the loop and tensioned for ending the operation to repair the cord. The artificial cord (7) is therefore attached to the papillary (8) and to the leaflet (2a) via staples (9).

According to a second example not shown, artificial cord (7), which has the form of a non-resorbable suture thread of polyamide or Teflon, may be notched. In this configuration, the staple (9) of the second assembly (13) may comprise any appropriate means, such as a pawl, for sliding along said notched artificial cord (7) and only in the direction of the staple (9) from the first assembly (6). In other words, when the second staple (9) is anchored on the leaflet (2a), the tension in the artificial cord (7) is adjusted by sliding the second staple (9) along the notched artificial cord (7).

The anchoring of the second staple (9) on the leaflet (2a) of the valve (2) can be improved via a stabilizing clip, not shown, similar to the clip (16) which will be described below. For this purpose, the second assembly (13) comprises such a clip pivotably connected to the end of the second rod (14) so as to pass, under the action of the control means, from a position folded back along the rod (14) to a position swung regularly to the rod (14), meaning parallel to the leaflet (2a) of the valve (2), and from an open position to a closed position for clamping and stabilizing the leaflet (2a) in order for anchoring the second elastic staple (9).

The attachment of the artificial cord (7) to the leaflet (2a) of the valve (2) may be done differently. In fact, referring to FIGS. 16 to 28, instead and in place of the second staple (9), the attachment means of the second assembly (13) may comprise a clip (16) connected pivotably to the end of the second rod (14) so as to pass, under the action of the control means, from a position folded back along the rod (14) (see FIG. 22) to a position swung angularly (see FIGS. 16 to 18, 21 and 23 to 27), in particular parallel to the leaflet (2a) of the valve (2). This clip (16) is designed to pass from an open position to a closed position for clamping the leaflet (2a), by the action, for example, of push and/or push cables. The clip (16) is connected to the artificial cord (7) for sliding along it during the insertion of the second assembly (13) into the left atrium (3) of the heart (4). For this purpose, the clip (16) comprises an upper jaw (16b), and a lower jaw (16a) equipped with a flap (17) articulated in order to adopt a closed position (see FIGS. 22 to 26) wherein it tightens and holds the artificial cord (7), while also allowing the sliding of the clip (16) around and along said artificial cord (7), and an open position (see FIGS. 21 and 27) for release of the artificial cord (7).

FIGS. 21 to 28 show the various steps implemented by the device in the steps shown in FIGS. 16 to 20. With reference to these figures, the clip (16) is intended to come clamp the leaflet (2a) (see FIGS. 17 and 24), while also being connected to the artificial cord (7). The jaws (16a, 16b) of the clip (16) both have openings to allow a needle (18), which is arranged inside the length of the second manipulation rod (14), to move to come pierce and pass through the thickness of the leaflet (2a) of the valve (2) (see FIG. 25).

Figure 25:
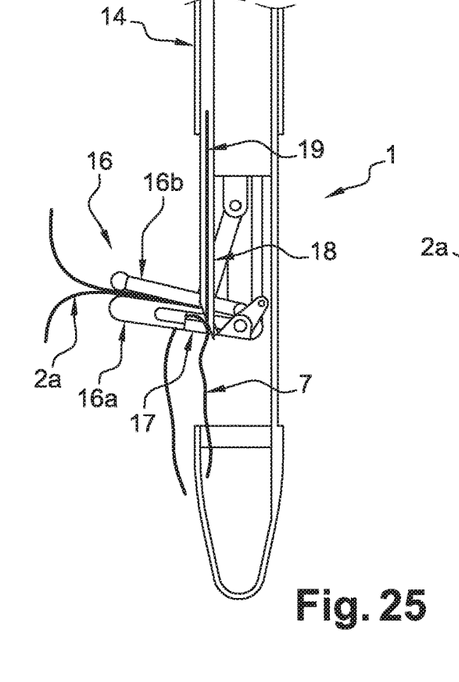
FIG. 25 is a view similar to that of FIG. 24, where a needle has been moved for piercing the mitral valve leaflet.
Figure 26:
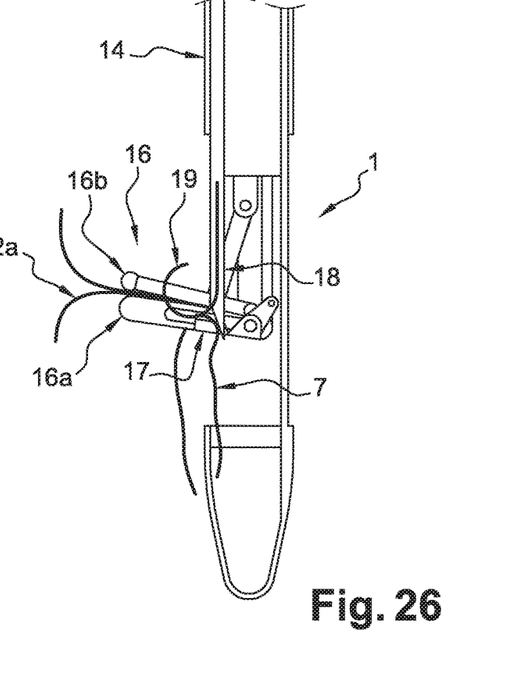
FIG. 26 is a view similar to that of FIG. 25, where a suture was extracted to form a loop around the artificial cord and through the leaflet.
Figure 27:
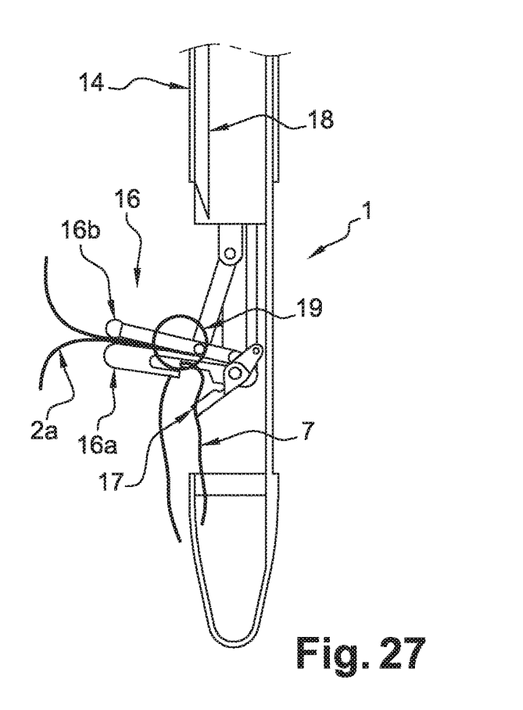
FIG. 27 is a view similar to that of FIG. 26, where the needle has been withdrawn and the artificial cord has been released by the clip.
Figure 28:
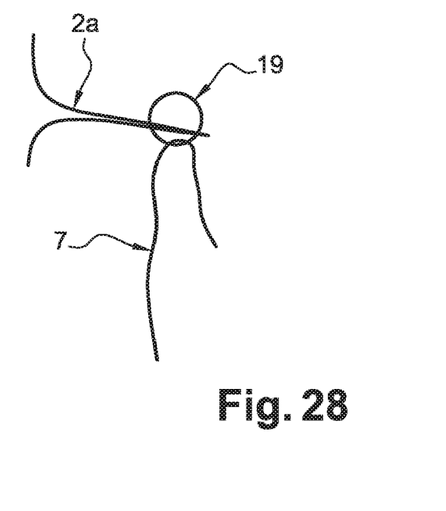
FIG. 28 is a view similar to that of FIG. 27, where the manipulation rod of the second assembly has been withdrawn and the artificial cord is attached to the leaflet via the shape memory suture.

The needle (18) serves to attach the artificial cord (7) to the leaflet (2a) of the mitral valve (2). To do that, the needle (18), after having passed through the leaflet (2a), can grab the artificial cord (7) held by the flap (17) and can be withdrawn to pass the artificial cord (7) through said leaflet (2a) for its attachment, in particular by knotting. The needle (18) therefore has means for grabbing the artificial cord (7), for example in the form of an inclined notch forming a hook at the end of the needle (18).

According to another technique, shown in FIGS. 18 to 20 and 26 to 28, the needle (18) has on the inside a shape memory suture (19), extractable for passing through the thickness of the leaflet (2a), and forming a loop, again passing through the thickness of the leaflet (2a), for attaching the artificial cord (7) to said leaflet (2a).

In this configuration, and with reference to FIGS. 19-20 and 27-28, the artificial cord (7) is attached to the papillary muscle (8) via a staple (9), and to the leaflet (2a) by means of a shape memory suture (19), forming a loop.

The characteristics of the device (1) according to the invention provide many advantages over existing solutions. Using the transfemoral approach reduces the duration and invasiveness of the procedure. It should be noted that the staples (9) and the clips (16) used are radio opaque, or else comprise radio opaque and/or ultrasound markers so that the surgeon can do a two-dimensional or three-dimensional check of their position as the operation progresses. Advantageously, the staples (9) used have textile sheaths to improve their rehabilitation by human tissue.

What is claimed is:

1. A device for repair of a ruptured cord of a mitral valve of a heart by transfemoral approach, said device configured to be positioned in a sealed inserter sized and shaped to be inserted into a femoral vein (transfemoral percutaneous access) and into a left atrium of the heart by passing through a septal wall of the heart (transseptal), wherein said device comprises:

a first manipulation rod containing a first assembly CONFIGURED [CONNECTOR, OPENER, CLOSER] for placement and attachment of an artificial cord on a papillary muscle having the ruptured cord, said first assembly arranged at an end of the first manipulation rod and including a staple connected pivotably and removably at the end of the first rod, said staple pivotable from a position folded back along the first rod to an angular position relative to the first rod, said staple angular position configured to be in front of the ruptured cord, the first assembly including a pair of arms located between portions of said staple, said arms each configured to apply a force to a respective staple portion for opening the staple, whereby absence of the force allows closing of the staple onto the papillary muscle said staple being connected to an artificial cord which extends proximally into the first rod;

a second manipulation rod containing a second assembly for placement and attachment of the artificial cord to a mitral valve leaflet having the ruptured cord, the second assembly arranged at an end of the second manipulation rod and including an anchor configured to slide along the artificial cord, said anchor pivotably connected to the end of the second rod, said anchor pivotable from a position folded back along the second rod to an angular position relative to the second rod, said anchor angular position configured to be parallel to the mitral valve leaflet, where the anchor is configured to attach the artificial cord to the leaflet.

2. The device according to claim 1, wherein the anchor comprises an openable, repositionable and removable second staple having portions biased toward each other, said second assembly including a second staple opener located between said biased portions of said second staple, said second staple opener configured to apply a second force to each of said biased portions of said second staple for opening the second staple, whereby absence of the second force allows closing of the second staple for attaching the artificial cord to the leaflet.

3. The device according to claim 2, wherein the artificial cord is notched, and the second staple is slidable on the notched artificial cord only in the direction of the staple from the first assembly.

4. The device according to claim 3, said notches on the artificial cord define means for sliding the second staple on the artificial cord only in the direction of the staple from the first assembly.

5. The device according to claim 2, wherein the second staple includes a thread configured to form an attachment loop around the artificial cord, where the artificial cord is knottable around said loop.

6. The device according to claim 2, wherein the second assembly includes a stabilizing clip connected pivotably to the end of the second rod said stabilizing clip pivotable from a position folded back along the second rod to an angular position relative to the second rod, said stabilizing clip angular position configured to be parallel to a plane of the leaflet, and said stabilizing clip configured to anchor said second staple by clamping onto and stabilizing the leaflet.

7. The device according to claim 6, further including control means, wherein said pivoting of said stabilizing clip from said folded back position to said angular position is actuated by said control means.

8. The device according to claim 2, said staple opener defining at least one of means for opening the second staple and means for unlocking the second staple.

9. The device according to claim 1, wherein the anchor comprises a clip connected pivotably to the end of the second rod, said clip pivotable from a position folded back along the second rod to an angular position relative to the second rod, said clip angular position configured to be parallel to a plane of a tissue of the leaflet, said clip having an open position and a closed position for clamping onto the leaflet, the second assembly including a needle movable through an opening in the clip, said needle configured to pierce the leaflet and attach the artificial cord to the leaflet.

10. The device according to claim 9, wherein a shape memory suture is positioned within said needle, said suture extractable from said needle to form a loop for attaching the artificial cord to the leaflet.

11. The device according to claim 9, wherein the needle includes a notch for grasping the artificial cord after having pierced the leaflet.

12. The device according to claim 11, wherein said notch defines means for grasping the artificial cord after said needle has pierced the leaflet.

13. The device according to claim 9, wherein the clip comprises an upper jaw and a lower jaw, with openings for the passage of the needle, the lower jaw, including a flap configured to adopt a closed position for holding the artificial cord while allowing the sliding of the clip around and along said artificial cord, and an open position for release of the artificial cord.

14. The device according to claim 9, wherein said clip defines attachment means for attaching the clip to the artificial cord.

15. The device according to claim 9, further including control means, wherein said moving of said needle through the opening in the clip is actuated by said control means.

16. The device according to claim 1, wherein the staple includes two elastic branches biased towards each other, said branches each having a hooked end, wherein said staple opener comprises two arms arranged between the elastic branches and articulated around a pivot to move said arms from a first position adjacent to each other to a separated second position at which said arms force apart the branches of the staple to cause opening of the staple, the arms being retractable to allow the staple to return to the biased, closed position.

17. The device according to claim 1, further including control means for actuation of said first assembly and actuation of said second assembly;
    wherein said pivoting of said staple from said folded back position to said angular position is actuated by said control means;
    wherein said opening of said staple and said closing of said staple onto the papillary muscle are each actuated by said control means;
    wherein said pivoting of said anchor from said folded back position to said angular position is actuated by said control means; and
    wherein said attaching of said anchor to the artificial cord is actuated by said control means.

18. The device according to claim 1, said pair of arms defining at least one of means for opening said staple and means for unlocking the staple.

19. The device according to claim 1, said anchor defining attachment means for attaching the artificial cord to the leaflet.

20. The device according to claim 1, wherein at least one of:
    said staple angular position is perpendicular in front of the papillary muscle; and
    said anchor angular position is parallel to the mitral valve leaflet.

* * * * *